(12) United States Patent
Ehwald et al.

(10) Patent No.: US 8,235,936 B2
(45) Date of Patent: Aug. 7, 2012

(54) MICRO-DIALYSIS PROBE

(75) Inventors: Rudolf Ehwald, Berlin (DE); Uwe Beyer, Bern (CH); Andreas Thomas, Prina (DE)

(73) Assignee: Roche Diagnostics International AG, Steinhausen (CH)

( * ) Notice: Subject to any disclaimer, the term of this patent is extended or adjusted under 35 U.S.C. 154(b) by 0 days.

(21) Appl. No.: 12/951,391

(22) Filed: Nov. 22, 2010

(65) Prior Publication Data

US 2011/0066103 A1     Mar. 17, 2011

Related U.S. Application Data

(63) Continuation of application No. 11/342,946, filed on Jan. 30, 2006, now Pat. No. 7,918,818, which is a continuation of application No. 10/068,670, filed on Feb. 5, 2002, now Pat. No. 7,008,398, which is a continuation of application No. PCT/CH00/00389, filed on Jul. 18, 2000.

(30) Foreign Application Priority Data

Aug. 6, 1999   (DE) .................................. 199 37 099

(51) Int. Cl.
    *A61M 3/00*   (2006.01)
(52) U.S. Cl. ........................................................ 604/43
(58) Field of Classification Search .............. 604/26–29, 604/43, 93, 96, 264, 44, 113, 366, 523, 4.01, 604/5.01–5.04, 6.09, 6.16; 606/108, 193, 606/195
    See application file for complete search history.

(56) References Cited

U.S. PATENT DOCUMENTS

| | | | |
|---|---|---|---|
| 4,531,937 A | | 7/1985 | Yates |
| 4,694,832 A | | 9/1987 | Ungerstedt |
| 5,191,900 A | * | 3/1993 | Mishra ........................ 600/585 |
| 5,257,977 A | | 11/1993 | Eshel |
| 5,333,609 A | | 8/1994 | Bedingham et al. |
| 5,372,582 A | | 12/1994 | Skrabal et al. |
| 5,441,481 A | * | 8/1995 | Mishra et al. .................. 604/29 |
| 5,738,656 A | | 4/1998 | Wagner |
| 5,779,665 A | | 7/1998 | Mastrototaro et al. |
| 5,951,521 A | | 9/1999 | Mastrototaro et al. |
| 6,264,627 B1 | | 7/2001 | Liska et al. |
| 6,537,241 B1 | | 3/2003 | Odland |
| 7,008,398 B2 | | 3/2006 | Ehwald et al. |

FOREIGN PATENT DOCUMENTS

| | | |
|---|---|---|
| DE | 1471408 | 9/1961 |
| DE | 3342170 | 6/1984 |
| DE | 90 02 100.2 | 8/1990 |
| DE | 19714087 A1 | 10/1998 |
| GB | 2130916 | 6/1984 |
| WO | 96/14889 | 5/1996 |

* cited by examiner

*Primary Examiner* — Manuel Mendez
(74) *Attorney, Agent, or Firm* — Dinsmore & Shohl, LLP

(57) ABSTRACT

A micro-dialysis probe extending longitudinally between a proximal probe opening and a distal probe tip and having a supply line and a drainage line for a drip-feed solution. A tube may be provided for supporting the drainage line. A dialysis section, wherein the flow channel for the drip-feed solution experiences an inversion, is formed generally between the supply line and the drainage line, in the vicinity of the distal probe tip. The supply line and the drainage line are respectively arranged substantially side by side and together form the probe shaft of the micro-dialysis probe.

35 Claims, 2 Drawing Sheets

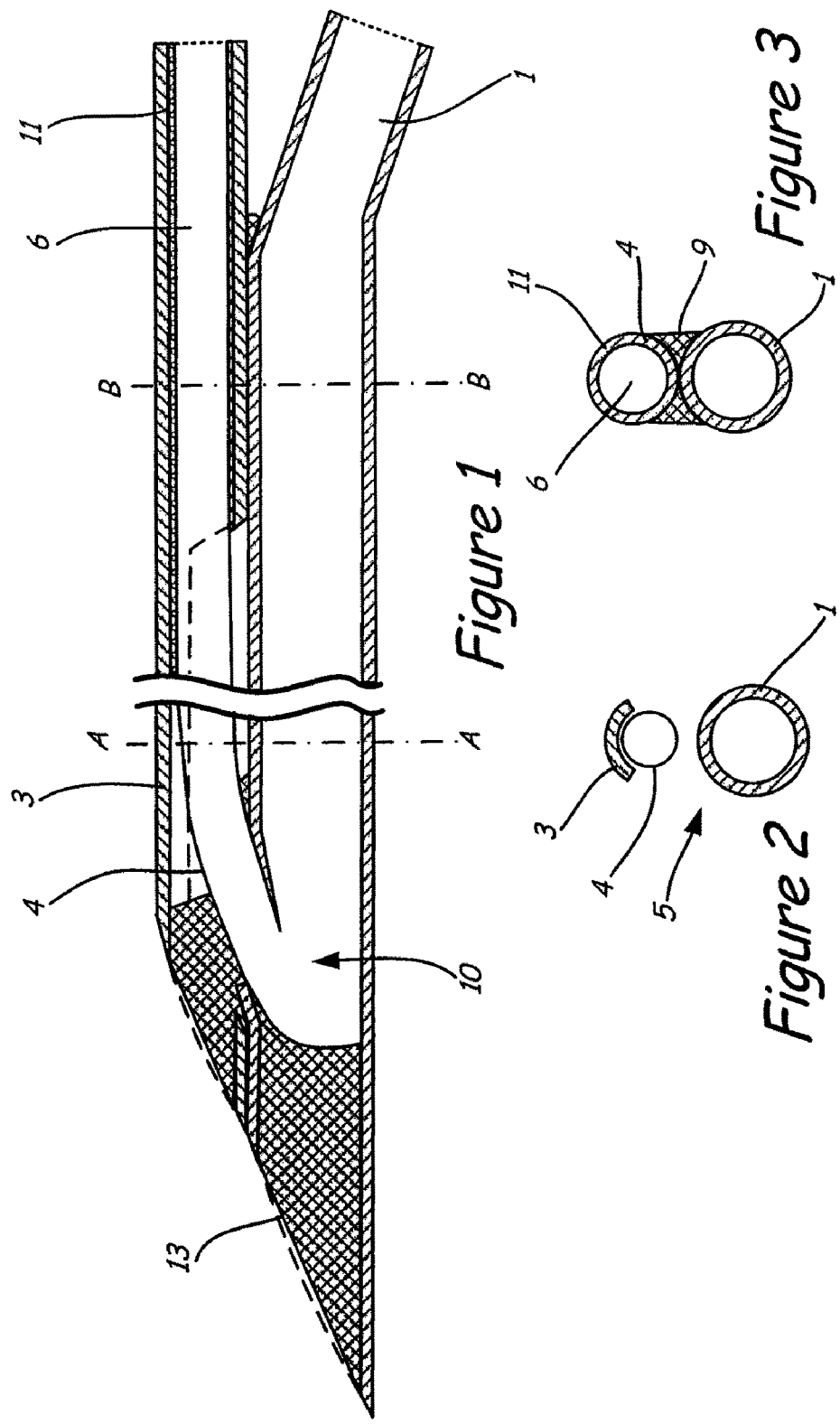

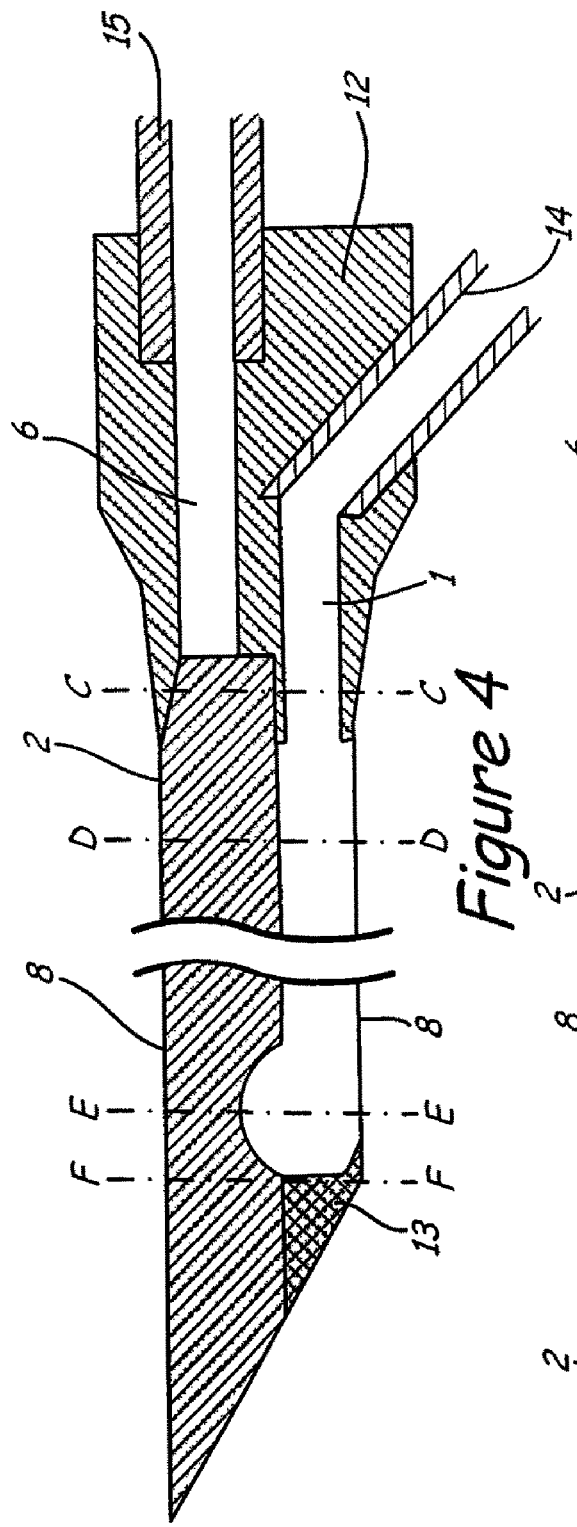
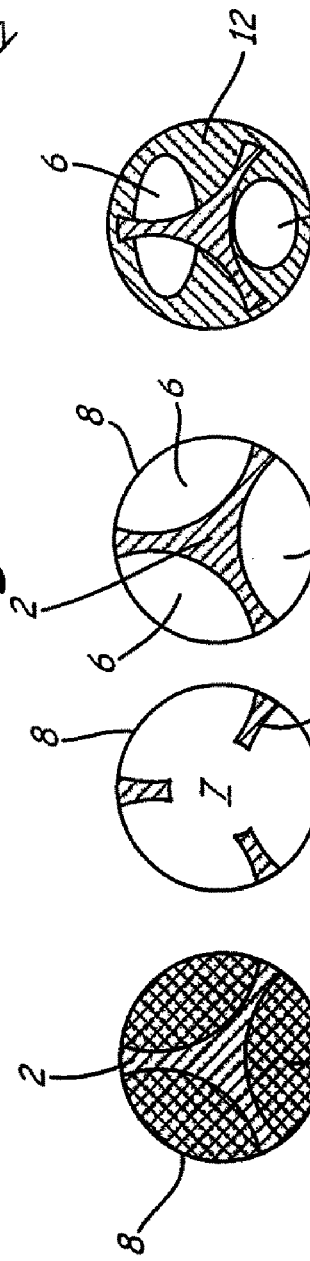

MICRO-DIALYSIS PROBE

PRIORITY CLAIM

This application is a continuation of U.S. patent application Ser. No. 11/342,946, filed Jan. 30, 2006, which is a continuation of U.S. patent application Ser. No. 10/068,670, filed on Feb. 5, 2002, issued as U.S. Pat. No. 7,008,398 on Mar. 7, 2006, which is a continuation of International Application No. PCT/CH00/00389, filed on Jul. 18, 2000, which claims priority to German Application No. 199 37 099 C2, filed on Aug. 6, 1999, each of which are herein incorporated by reference in their entirety.

TECHNICAL FIELD

The present invention relates to micro-dialysis probes and, more particularly, to a micro-dialysis probe including a supply line and a drainage line for a dip-feed solution and a dialysis section, wherein the flow channel for the dip-feed solution experiences an inversion in the area of the dialysis solution between the supply line and drainage line. Implanted hollow fibers, hollow fiber loops or dialysis probes are used for micro-dialysis in medicine and biological research. Conventional dialysis probes possess a tube-shaped shaft in which dialysate is drained and which comprises a closed cylindrical membrane (hollow fiber sealed on one side) into whose interior a thin tube protrudes, for supplying the drip-feed solution. Between the drip-feed solution flowing back and the ambient medium, dialysis at the hollow fiber membrane leads to a concentration equalization in the permeable substances. Probes with the same principle design are also known, in which the dialysis fiber is surrounded by a non-buckling casing or framework which it partially protrudes out from, said dialysis fiber being supported by said casing or framework. Such a dialysis probe is known, for example, from DE 33 42 170 C2.

In use of viscous drip-feed solutions or at high flow rates in particular, it is evident that the flow through such dialysis probes in not optimal. Lateral pressure upon the probe can move the inner tube slightly our of its central position and the flow profiles via the hollow cylinder are changed. The flow can slow up or come very narrow, while a fast flowing preferential path forms on the opposite side. Moreover, a dead space arises in the shaft in which the dialysate is drained, due to its construction, at the transfer point into the drainage tube. Both of these lead to a delay in adjusting of the equilibrium.

To stabilize the position of the inner tube in the hollow fiber, DE 197 14 087 A1 has proposed, for such probes, surrounding the capillary with a profile. Profiles with such a small diameter and a central bore, however, can only be produced at great cost.

SUMMARY OF THE INVENTION

The present invention relates to a dialysis probe having a supply line and a drainage line for a drip-feed solution and a dialysis section arranged generally therebetween. The dialysis probe is configured such that solution flowing from the supply line to the drainage line experiences an inversion in flow in the area of the dialysis section. Thus, the dialysis probe of the present invention provides stable flow guidance and thus a fast adjustment of the equilibrium. Further, in the dialysis probe of the present invention, flow-impeding dead spaces in the dialysis section and in the supply line and drainage line are substantially avoided.

The supply line and drainage line are thus arranged generally side by side in accordance with the invention, not one inside the other as in the prior art. Thus, the supply line and the drainage line together form a probe and can thus, through their own structure or by providing protective devices formed thereover, be stably developed such that mechanical influences do not impede the flow of the drip-feed solution. While in the prior art, for example in accordance with DE 33 42 170 C2, pressure on the outer hollow cylinder (i.e., the drainage line) automatically affects the supply line within it, outside pressure on the probe does not similarly affect the supply line and drainage line of the invention.

A further advantage of the dialysis probe in accordance with the invention is that the supply line and drainage line can each simply run straight in or out of the rear part of the dialysis probe, and flow redirection in which dead spaces are formed can be largely avoided.

In an embodiment of the micro-dialysis probe in accordance with the invention, the first drainage line in the direction of the flow consists of a dialysis hollow fiber penetrating into the supply line behind the inversion, the hollow fiber being fastened in the area of the sealed tip of the probe such that a linear course of flow is achieved after the inversion, while at its other end it is sealed into a second stable section of the drainage line. In this way, the drip-feed solution flows through the whole cross-section of the dialysis hollow fiber in one direction, and the dialysate is introduced into the drainage line linearly, without a change in direction. The flow direction is here inverted as necessary to enable the liquid to be supplied and drainage from one side, before it enters the dialysis hollow fiber, such that the dialysis itself is not impeded by disturbances in the flow. The previously mentioned stable section is preferably a tube which forms the outer part of the drainage line, i.e. its supporting component. In this way, the part of the tube in the area of the tip of the probe which lies over the hollow fiber, where the dialysis hollow fiber penetrates into the supply line, can form a supporting section to mechanically strengthen this part of the probe.

The hollow fiber is preferably formed to be replaceable; and correspondingly sealed in, the tube in particular its supporting section comprising recesses via which the hollow fiber is exposed outwards, to be able to perform dialysis. In this way, the supply line, and the supporting section arranged on the opposite side of the hollow fiber parallel to said supply line, form an outer framework which mechanically shields the hollow fiber from the surrounding matrix of tissues without preventing direct liquid contact between the hollow fiber and the surrounding medium. The supply line and the drainage line can in principle be separate parts, connected firmly at the tip and the side facing away from it, when assembled. However, it is particularly favorable if the supply line and the drainage line, which comprise a flow connection in their tip, are integrated into a single piece, for example via a fixing material.

In a further preferred embodiment of the micro-dialysis probe in accordance with the invention, the flow channel for the drip-feed solution consists of a hollow fiber with a supporting profile inserted into it which separates the supply line and the drainage line from each other, the supporting profile comprising overflow openings in the area of flow inversion. Here too, therefore, the principle is again realized that each of the supply line and the drainage line form, together with the hollow fiber, a part of the outer wall of the probe, but are separated and supported in such a way that the flow is not impeded. In this way, both the supporting function and flow guidance are assumed by the profile. The supporting profile is thus designed in accordance with the invention such that the volume of the hollow fiber through which the flow may pass consists of a number of elongated hollow spaces. These hollow spaces enable the drip-feed agent to flow into the tip of the probe and to be re-circulated to the other side, wherein the flow is inverted by the overflow openings. Here, too, the flow in and out can largely be achieved in a straight course of flow.

An embodiment of the micro-dialysis probe as described above is preferred developed such that the hollow fiber at the supply line end and drainage line end of the probe is sealed into a probe shaft which accommodates and continues the supply line and the drainage line separately. Such a probe shaft ensures a further increase in stability and enables the necessary connections to be provided.

The supporting profile can be developed with a star-shaped cross-section, for example as a three- or four-armed star. On the other hand, however, it is also possible to form the profile as a flat partition which exhibits a rectangular or lenticular cross-section and is provided on one or both of its flat sides with fine bristles or knobs which keep the hollow fiber wall at a distance.

The greatest mechanical stability, however, is achieved using a star profile. In the case of a four-armed star profile, the drip-feed solution is guided in two parallel channels as the supply line, while the other two channels form the drainage line. If a three-armed star profile is used, the stretching of the hollow fiber material caused by swelling can be compensated for, if the dry hollow fiber is moved taut over the profile and appears in the cross-section like a triangle with rounded corners. When the hollow fiber membrane is stretched, this again forms a circle in cross-section. In this three-armed embodiment of the profile, a single supply line is accordingly provided, but two drainage lines. Since the hollow fiber is sufficiently supported from within, it can be exposed to the matrix of tissues along its entire length. Dialysis then takes place both in the supply line as well as the drainage lines.

Although a higher flow rate prevails in the individual supply line due to the smaller cross-section, and efficient exchange of material take also place here, since the concentration gradient between the drip-feed solution and the surroundings is still at its greatest in this area. After the drip-feed solution has overflowed into the two parallel drainage lines in the immediate vicinity of the tip, the flow rate is halved, which promotes concentration equalization between the substances passing through the hollow fiber, since more time is available for this purpose.

The supply line and/or drainage line of micro-dialysis probe in accordance with the invention should preferably have a substantially linear course, to largely rule out the formation of dead species in the flow.

BRIEF DESCRIPTION OF THE DRAWINGS

FIG. 1 illustrates a perspective view of a longitudinal section of a micro-dialysis probe in accordance with a first embodiment of the present invention.

FIG. 2 illustrates a cross-sectional view of the embodiment of FIG. 1, taken along A-A of FIG. 1.

FIG. 3 illustrates a cross-sectional view of the embodiment of FIG. 1, taken along B-B of FIG. 1.

FIG. 4 illustrates a perspective view of a longitudinal section of a micro-dialysis probe in accordance with a second embodiment of the present invention.

FIG. 5 illustrates a cross-sectional view of the embodiment of FIG. 4, taken along C-C of FIG. 4.

FIG. 6 illustrates a cross-sectional view of the embodiment of FIG. 4, taken along D-D of FIG. 4.

FIG. 7 illustrates a cross-sectional view of the embodiment of FIG. 4, taken along E-E of FIG. 4.

FIG. 8 illustrates a cross-sectional view of the embodiment of FIG. 4, taken along F-F of FIG. 4.

DETAILED DESCRIPTION OF THE DRAWINGS

FIG. 1 illustrates a micro-dialysis probe in accordance with a first embodiment of the present invention. The micro-dialysis probe extends longitudinally between a proximal probe opening and a distal probe tip. A supply line 1, or a supply channel, is provided through which the drip-feed solution is introduced into the probe. A drainage line 6, formed by a hollow fiber 4, is provided for draining the drip-feed solution from the probe. A tube 11 may be provided surrounding the drainage line 6 for supporting the drainage line 6. The hollow fiber 4 is may be formed to be replaceable, and correspondingly sealed in, the tube 11. The supply line 1 and drainage line 6 are arranged substantially side-by-side and together form the probe shaft of the micro-dialysis probe. At the distal probe tip the probe is sealed and pointed with a sealing material 13, to enable it to be introduced into subcutaneous tissue. In the vicinity of the probe tip, a dialysis opening 10 is provided in the supply line 10. The hollow fiber 4 penetrates from above into the dialysis opening 10 of the supply line 1. Flow connection between the supply line 1 and the hollow fiber 4 is thus formed with the aid of the shaping of the sealing material, such that the flow can be inverted without being substantially impeded. The hollow fiber 4 in the area of the opening 10 is sealed with the sealing material such that there is no leakage. Thus, the drip-feed solution flows through the whole cross-section of the dialysis hollow fiber in one direction and is introduced in the drainage line linearly without a change in direction. The flow direction is here inverted to enable the liquid to be supplied and drained from one side, before it enters the dialysis hollow fiber, such that the dialysis itself is not impeded by disturbances in the flow.

In the area of the flow inversion, a dialysis section is formed. To form the dialysis section the tube 11 surrounding the drainage line 6 is provided with recesses 5 in the area of the cross-sectional view of FIG. 2, such that the hollow fiber 4 is here exposed to the surrounding tissue and dialysis can take place. The supply line 1, and the supporting section of the tube 11 arranged on the opposite side of the hollow fiber 4 parallel to the supply line 1, form an outer framework which mechanically shields the hollow fiber 4 from the surrounding matrix of tissues without preventing direct liquid contact between the hollow fiber 4 and the surrounding medium. The supply line 1 and the drainage line 6 may be formed as separate parts, connected firmly at the distal probe tip and the proximal probe opening. However, in a preferred embodiment, the supply line 1 and the drainage line 6, having a flow connection, or dialysis section, near their tip, are integrated in a single piece.

Only one supporting section 3 of tube 11 lies over the hollow fiber 4 in this area, to shield said fiber on this side from mechanical pressure from without.

In its further course towards the proximal probe opening, opposite the probe tip, the hollow fiber 4 is again surrounded by the tube 11, as shown in the cross-sectional view of FIG. 3. In this area, the hollow fiber is sealed by a carrier material (shown in grey) in the tube 11. The supply line 1 and the drainage line 6 with the surrounding tube 11 are fixed to one another in this area using the fixing material 9, shown in FIG. 3. The dialysis probe thus forms an integral unit.

FIG. 4 illustrates a micro-dialysis probe of the present invention in accordance with a second embodiment. The flow channel for the drip-feed solution consists of a hollow fiber 8 with a supporting profile 2 inserted into it which separates the supply line 1 and the drainage line 6 from one another, the supporting profile 2 having at least one opening 7 in the area of flow inversion. The supply line 1 and drainage line 6, together with the hollow fiber 8, form a part of the outer wall of the probe, but are separated and supported such that the flow is not impeded. The supporting function and flow guidance are assumed by the profile 2. The supporting profile 2 is thus configured such that the volume of the hollow fiber 8 through which the flow may pass consists of a number of elongated hollow spaces. These hollow spaces enable the drip-feed solution to flow into the probe tip and to be re-circulated to the other side, wherein the flow is inverted by the overflow openings.

As shown in FIG. 4, the supply line channel 1 and drainage line channel 6 lie, proximal end of the probe, opposite the probe tip, in a probe shaft 12, where inserted hoses 14 and 15 are arranged. The probe shaft 12 accommodates and continues the supply line 1 and the drainage line 6 separately. The probe shaft 12 increases stability of the micro-dialysis probe. A profile 2 is attached to the left front face of the shaft 12, over which the hollow fiber 8 is pulled and sealed at the point of attachment. As shown, the profile has a three-armed star shape. The profile may alternately be shaped as a four-armed star or may be flat. If the profile is flat, it may exhibit a rectangular or lenticular cross-section and be provided on one or both of its flat sides with fine bristles or knobs to support the hollow fiber and maintain it at a distance. The supply line 1 and the drainage line 6 are formed in the area of the shaft 12 by the shaft itself, as shown in the cross-sectional view of FIG. 5. FIG. 6 is a cross-sectional view showing a lower supply line 1 and two upper drainage lines 6 being are formed by the profile 2 covered by the hollow fiber 8. The supply line 1 and the drainage line 6 are separated from one another, and extend generally in parallel. At the point of the micro-dialysis probe shown in FIG. 7, the center of the profile 2 is left open, such that an overflow opening 7 is created through which the drip-feed liquid can flow from the supply line 1 into the drainage lines 6, thereby creating a primary dialysis section. Thus, in this embodiment, flow inversion takes place here. Of course, the overflow opening can be formed at a different point in the micro-dialysis probe and need not correspond exactly with the cross-sectional point of FIG. 7. The profile is sealed together with the hollow fiber at the tip by a sealing material 13, as can be seen in FIG. 8. After passing the overflow opening 7, the drip-feed liquid flows into the two drainage lines 6, which re-unite in the area of the shaft. As shown, the supply line and the drainage lines run side by side and are supported from within by the profile 2, such that impedance of the flow through external influences is substantially prevented. In the embodiment shown, the flow is substantially linear and is guided in a generally straight line, such that dead spaces and the impedance of the flow and delays in adjusting the equilibrium associated therewith substantially avoided.

As discussed above, the profile may be formed in any suitable shape, for example as a three or four-armed star or as flat with a rectangular or lenticular cross-section. A star-shaped profile is preferred as it achieves high mechanical stability. Using a four-armed star profile, the drip-feed solution is guided in two parallel channels as the supply line, and two parallel channels as the drainage line. Using a three-armed star profile, the stretching of the hollow fiber material caused by swelling may be compensated for, if the dry hollow fiber is moved taut over the profile and appears in cross-section as a triangle with rounded corners. When the hollow fiber membrane is stretched, a circle cross-section is again formed. In the three-armed star embodiment of the profile, a single supply line and two drainage lines are provided. As the hollow fiber is supported from within, it may be exposed to the matrix of tissues along its entire length. Dialysis then takes place both in the supply line as well as in the drainage lines.

Dialysis takes place along the entire section of the hollow fiber 8, form the shaft 12 up to the sealing material 13, both in the supply line 1 and in the drainage lines 6. Because of the smaller cross-section, the solution admittedly flows faster in the supply line 1, however the highest concentration gradient is also present in this area, such that sufficient dialysis takes place. This concentration gradient is admittedly lower in the two drain line sections, however the contact areas here is even greater and the flow rate is only a half, such that the effective concentration equalization can also be achieved in this area. Components 14 and 15 can be developed as supply and drainage hoses respectively, and simply sealed into the shaft at their insertion points, such that the solution is prevented from escaping.

In the foregoing description preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principles and the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

We claim:

1. A micro-dialysis probe for introducing a solution into surrounding tissue, comprising:
   a probe shaft having a proximal end and a distal probe tip;
   a hollow fiber forming part of the probe tip, and forming a drainage line, the drainage line having a dialysis section for providing the solution to the surrounding tissue;
   a supply line for providing the solution to the drainage line, the supply line and drainage line being arranged as separate hollow channels which extend substantially side-by-side; and
   an opening provided between the supply line and the drainage line in the area of the dialysis section such that the solution which flows from the supply line into the drainage line in the area of the opening experiences a flow inversion.

2. The micro-dialysis probe of claim 1, further comprising a sealing material which both forms part of and seals the probe tip.

3. The micro-dialysis probe of claim 1, wherein the dialysis section is in the vicinity of the probe tip.

4. The micro-dialysis probe of claim 1, wherein the solution comprises a drip-feed solution.

5. The micro-dialysis probe of claim 1, further comprising a tube which surrounds a portion of the drainage line of the hollow fiber.

6. The micro-dialysis probe of claim 1, further comprising a tube in which the hollow fiber is sealed therein proximally of the area of the flow inversion.

7. The micro-dialysis probe of claim 1, wherein the drainage line penetrates into the supply line at the opening proximally of the area of the flow inversion, the drainage line being fixed in the area of the probe tip such that a linear course of flow is achieved distal of the area of the flow inversion.

8. The micro-dialysis probe of claim 1, wherein the supply line and the drainage line are fixed to one another using a fixing material in an area between the opening and the dialysis section.

9. The micro-dialysis probe of claim 1, further including a tube surrounding at least the drainage line, the tube having recesses to expose the drainage line to surrounding tissue in the vicinity of the probe tip.

10. The micro-dialysis probe of claim 1, further comprising a tube wherein a section of a tube lies over the drainage line in the area of the probe tip which forms a supporting section for the drainage line.

11. The micro-dialysis probe of claim 1, further comprising a tube wherein the supply line and tube together form an outer framework that shields the drainage line from the surrounding tissues.

12. The micro-dialysis probe of claim 1, wherein the hollow fiber forms both part of the supply line and the drainage line.

13. The micro-dialysis probe of claim 1, further comprising a supporting profile which forms part of the probe tip.

14. The micro-dialysis probe of claim 1, wherein the hollow fiber is pointed at the probe tip.

15. The micro-dialysis probe of claim 1, further comprising a supporting profile provided in the hollow fiber to form both another part of the supply line and the drainage line.

16. The micro-dialysis probe of claim 1, wherein the drainage line comprises two drainage channels which re-unite adjacent the proximal end of the probe shaft.

17. The micro-dialysis probe of claim 1, further comprises a supply hose provided to the probe shaft and fluidly connected to the supply line.

18. The micro-dialysis probe of claim 1, further comprises a drainage hose provided to the probe shaft and fluidly connected to the drainage line.

19. The micro-dialysis probe of claim 1, wherein the dialysis section extends from the probe shaft to the probe tip.

20. The micro-dialysis probe of claim 1, wherein the hollow fiber also forms part of the supply line.

21. The micro-dialysis probe of claim 1, wherein the hollow fiber also forms part of the supply line, the supply line also having a dialysis section.

22. The micro-dialysis probe of claim 1, wherein the hollow fiber also forms part of the supply line, the supply line also having a dialysis section, and wherein the dialysis section of each the supply line and the drainage line extends from the probe shaft to the probe tip.

23. The micro-dialysis probe of claim 1, wherein the hollow fiber is replaceable.

24. The micro-dialysis probe of claim 1, wherein the hollow fiber extends longitudinally between the proximal end and the distal probe tip.

25. The micro-dialysis probe of claim 1, wherein a tube surrounds the drainage line for supporting the drainage line.

26. The micro-dialysis probe of claim 1, further comprising a sealing material which both forms part of the probe tip and defines part of the opening.

27. The micro-dialysis probe of claim 1, further comprising a sealing material and a supporting profile both provided in the hollow fiber to form both another part of the supply line and the drainage line and to define the opening.

28. The micro-dialysis probe of claim 1, wherein the hollow fiber forms a part of both the drainage line and the supply line as well as an outer wall of the probe.

29. The micro-dialysis probe of claim 1, further comprising a supporting profile provided in the hollow fiber and configured such that the volume of the hollow fiber through which the flow of the solution passes consists of a number of the separate hollow channels.

30. The micro-dialysis probe of claim 1, further comprising a supporting profile provided in the hollow fiber and having a three-armed star shape or a four-armed star.

31. The micro-dialysis probe of claim 1, further comprising a supporting profile provided in the hollow fiber and having a flat shape with a rectangular cross-section or a lenticular cross-section, and being provided on one or both of its flat sides with fine bristles or knobs to support the hollow fiber.

32. The micro-dialysis probe of claim 1, wherein the probe shaft forms part of the supply line and the drainage line.

33. The micro-dialysis probe of claim 1, further comprising a supporting profile provided in the hollow fiber, wherein a center of the supporting profile defines the opening.

34. The micro-dialysis probe of claim 1, further comprising a supporting profile provided in the hollow fiber and a sealing material, wherein the profile is sealed together with the hollow fiber at the probe tip by the sealing material.

35. The micro-dialysis probe of claim 1, wherein the hollow fiber is configured to be exposed to the surrounding tissue along its entire length.

* * * * *

UNITED STATES PATENT AND TRADEMARK OFFICE
CERTIFICATE OF CORRECTION

PATENT NO. : 8,235,936 B2
APPLICATION NO. : 12/951391
DATED : August 7, 2012
INVENTOR(S) : Rudolph E. Ehwald et al.

It is certified that error appears in the above-identified patent and that said Letters Patent is hereby corrected as shown below:

In the Specifications:

Col. 1, Line 41, "probes in not optimal" should read -- probes is not optimal --

Col. 1, Line 42, "slightly our of its" should read -- slightly out of its --

Col. 2, Line 1, "line are thus arranged" should read -- line are arranged --

Signed and Sealed this
Thirtieth Day of April, 2013

Teresa Stanek Rea
*Acting Director of the United States Patent and Trademark Office*